United States Patent [19]

Bedi

[11] Patent Number: 5,513,635
[45] Date of Patent: May 7, 1996

[54] NASAL CANNULA ANCHORING APPARATUS

[76] Inventor: Shan Bedi, 801 N. Third St., Burlington, Iowa 52601

[21] Appl. No.: 382,564
[22] Filed: Feb. 2, 1995
[51] Int. Cl.$^6$ ............................ A61M 15/08; A61M 5/32
[52] U.S. Cl. ............................ 128/207.18; 128/DIG. 26; 604/180
[58] Field of Search ................... 128/207.17, 207.18, 128/DIG. 26; 604/174, 179, 180

[56] References Cited

U.S. PATENT DOCUMENTS

| | | | |
|---|---|---|---|
| D. 243,477 | 2/1977 | Cutruzzula et al. | D24/128 |
| 3,046,989 | 7/1962 | Hill | 128/207.19 X |
| 3,288,136 | 11/1966 | Lund | 128/207.18 |
| 3,430,300 | 3/1969 | Doan | 24/304 |
| 4,120,304 | 10/1978 | Moor | 604/180 |
| 4,324,236 | 4/1982 | Gordon et al. | 128/DIG. 26 X |
| 4,454,880 | 6/1984 | Muto et al. | 128/205.25 |
| 4,490,141 | 12/1984 | Lacko et al. | 604/180 |
| 4,534,762 | 8/1985 | Heyer | 604/180 |
| 4,738,662 | 4/1988 | Kalt et al. | 604/180 |
| 4,804,374 | 2/1989 | Laskody | 604/180 |
| 4,823,789 | 4/1989 | Beising | 128/207.18 |
| 5,135,506 | 8/1992 | Gentelia et al. | 604/180 |
| 5,156,641 | 10/1992 | White | 128/207.18 |
| 5,172,688 | 12/1992 | Dillon | 128/207.18 |
| 5,308,339 | 5/1994 | Kalt et al. | |

FOREIGN PATENT DOCUMENTS

| | | | |
|---|---|---|---|
| 503739 | 6/1964 | Canada | 128/207.18 |
| 2251796 | 7/1992 | United Kingdom | 128/207.18 |

Primary Examiner—Edgar S. Burr
Assistant Examiner—Eric P. Raciti
Attorney, Agent, or Firm—Henderson & Sturm

[57] ABSTRACT

A nasal cannula anchor that includes a body engaging portion that is adapted to adhere to the nose of a subject; and two cannula engaging portions extending from the body engaging portion that are adapted to anchor a cannula. A method for anchoring a length of cannula in the nose of a subject that involves adhering a structure comprising a body engaging portion to the nose of a subject; and wrapping two cannula engaging portions extending from the body engaging portion of the structure around a section of length of a cannula to anchor said cannula.

11 Claims, 3 Drawing Sheets

NASAL CANNULA ANCHORING APPARATUS

TECHNICAL FIELD

The present invention relates to the field of anchoring apparatus and devices for cannula, and more particularly to anchoring apparatus for nasal cannula. More specifically, the present invention is directed to a nasal cannula anchor that has a novel shape for anchoring a nasal cannula in place on the nose of a subject or patient. Specifically, the present invention is directed to a nasal cannula anchor which is constructed to have a two-legged "octopus" formation having a body engaging portion that is adapted to be attached onto the nose of a subject, and two legs as tube engaging portions that are adapted to be anchored to the side of a tube, such as an oxygen cannula, i.e., a nasal cannula. The nasal cannula anchor is provided with an adhesive surface on one side for attaching its body engaging portion to the nose of the subject, and for attaching its tube engaging portions when wrapped around the tube so as to anchor the oxygen tube to the nasal cannula anchor.

BACKGROUND ART

Prior to the present invention, it is not believed that the prior art included a nasal cannula anchor having a two-legged "octopus" formation, including a body for tagging onto the nose of a patient, and two legs which are adapted to be anchored to the side of an oxygen cannula.

SUMMARY OF THE INVENTION

The present invention is directed to a nasal cannula anchor which is constructed to have a two-legged "octopus" formation which has a body that is adapted to be attached onto the nose of a subject, and two legs that are adapted to be anchored to a tube, such as an oxygen cannula, and wherein the nasal cannula anchor is provided with an adhesive surface on one side for attaching it to the nose, and also for attaching to itself so as to anchor the oxygen tube.

DETAILED DESCRIPTION

The following is a detailed description of the present invention that is intended to be claimed.

Figure 1:
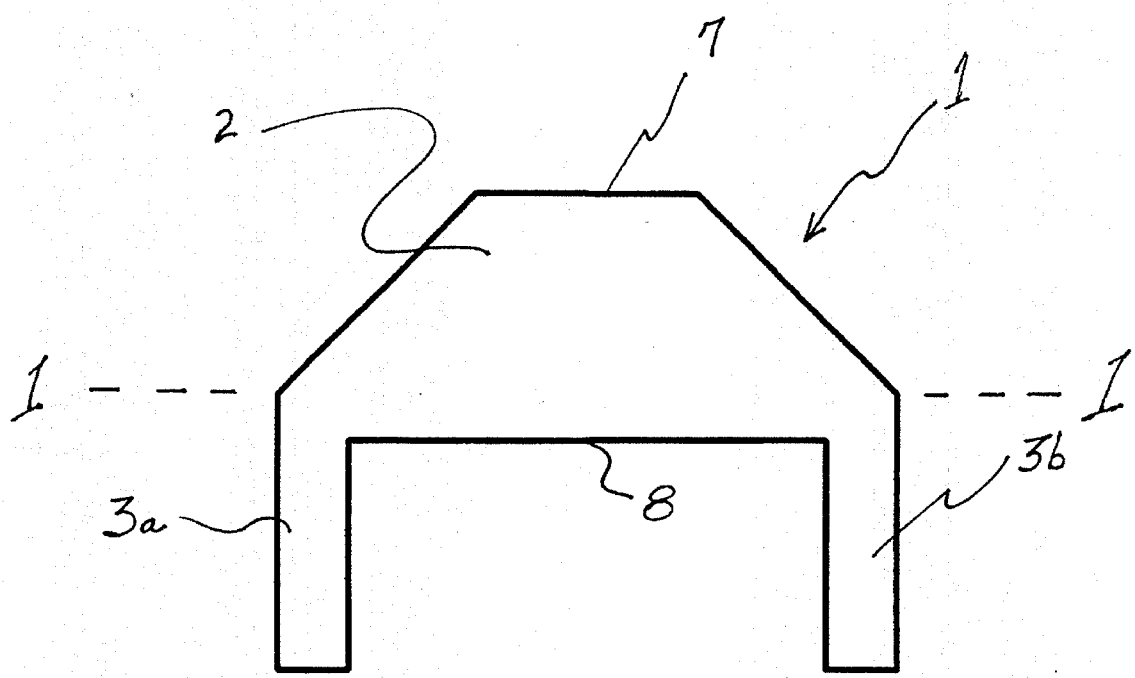
FIG. 1 depicts a top view of a nasal cannula anchor apparatus in accordance with the present invention.

As generally shown in FIG. 1, the present invention is directed to a nasal cannula anchor 1 which is constructed to have a novel shape, referred to herein as two-legged "octopus" formation or shape, that includes a body, body portion, or body engaging portion 2, that is adapted to be tagged, engaged, or otherwise adhered to the nose of a subject or patient; and two legs 3a and 3b, also referred to herein as cannula engaging portions 3a and 3b, that are adapted to be engaged, wrapped, or otherwise adhered or to a tube or cannula, such as an oxygen cannula.

More specifically, the nasal cannula anchor of the present invention includes a structure for anchoring a length of cannula to the nose of a subject, wherein such structure includes a body engaging portion 2 that is adapted to adhere to the nose of a subject; and two cannula engaging portions 3a and 3b extending from the body engaging portion that are adapted to anchor a cannula. As shown in FIG. 1, the body engaging portion 2 comprises a substantially curved leading edge 7 adapted to be oriented towards the bridge of the nose of the subject when the body engaging portion is adhered to the nose of the subject. The body engaging portion 2 also has a trailing edge 8 opposite the substantially curved edge 7 adapted to be oriented away from the bridge of the nose when the body engaging portion is adhered to the nose of the subject. As shown, the trailing edge 8 includes a substantially straight central section adapted or otherwise configured to be clear of nasal passages when the body engaging portion 2 is adhered to the nose of the subject. The two cannula engaging portions 3a and 3b, preferably extend from the body engaging portion 2 substantially as shown in FIG. 1, and are separated from each other by the straight central section of said trailing edge 8.

The nasal cannula anchor 1 includes a patch layer 4 that is composed of suitable material for allowing the body engaging portion 2 to cover a portion of the nose of a subject, and the two legs or tube engaging portions 3a and 3b to be wrapped or otherwise secured around a tube, such as an oxygen cannula. Suitable materials for the patch layer 4 for purposes of the present invention, include polyethylene films.

The body engaging portion 2 and cannula engaging portions 3a and 3b of the nasal cannula anchor 1 of the present invention are adapted to be attached to the nose of a subject or patient, and a tube, respectively. For purposes of the present invention, the nasal cannula anchor 1 is provided with a suitable structure for adhering the body engaging portion 2 of the patch layer 4 to the nose of the subject and for adhering the cannula engaging portions 3a and 3b to a tube. In accordance with the present invention, such suitable structure includes means for adhesion. For purposes of the present invention, the patch layer is provided with a suitable adhesive over at least a portion of its engaging surface, i.e., its one side for attaching it to the nose, and also for attaching it to the tube. The adhesives employed for purposes of the present invention are non-allergenic (hypoallergenic) adhesives, such as those conventionally used with various forms of bandages and wound dressings that are non-irritating to dermal tissue and do not deteriorate when exposed to water and/or body fluids. A hypoallergenic acrylic adhesive is particularly suitable for purposes of the present invention. Preferably, the patch layer is coated over substantially its entire engaging surface with the adhesive that forms an adhesive layer 5.

Figure 2:
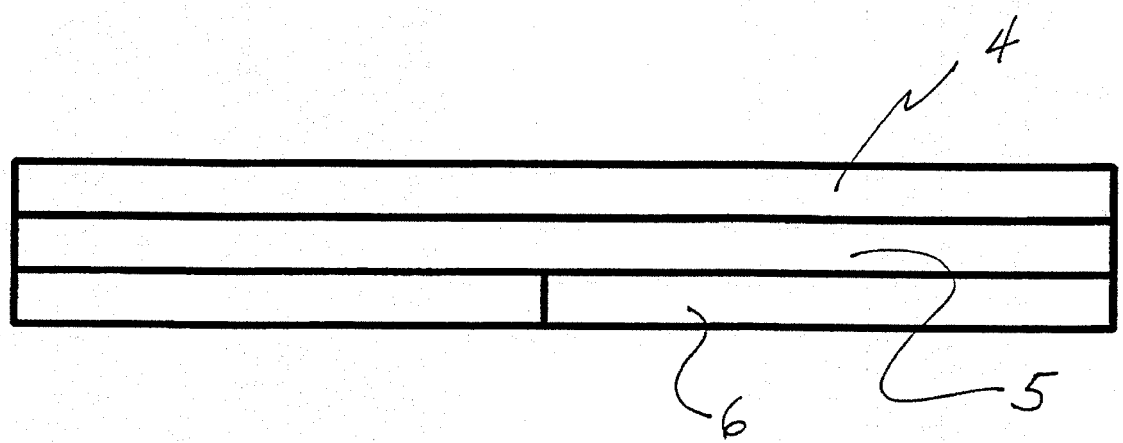
FIG. 2 depicts a cross sectional view of a nasal cannula anchor apparatus in accordance with the present invention.
Figure 3:
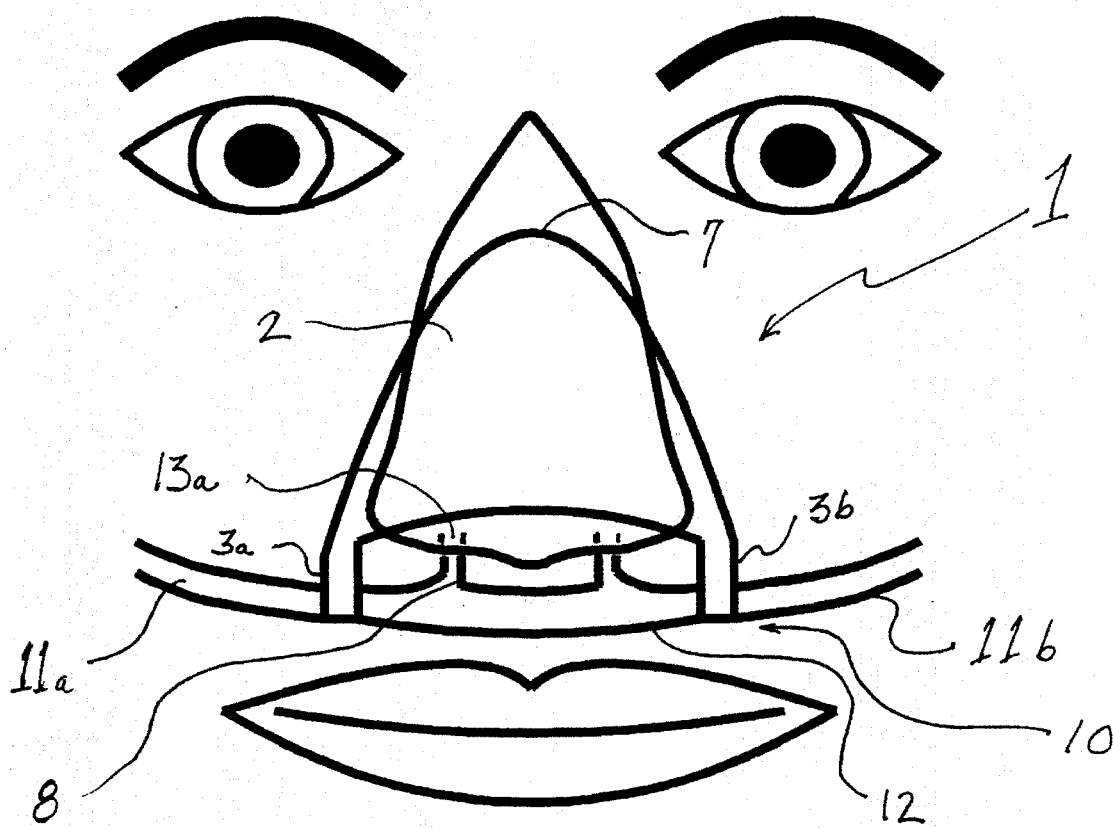
FIG. 3 depicts a nasal cannula anchor apparatus in accordance with the present invention anchoring a nasal cannula depicted as inserted in the nostrils of a subject.

The adhesive layer 5 is preferably covered with a peel layer 6 that is made of suitable material to function as a protective layer, particularly for the adhesive layer, that is designed to be removed before applying the patch. The peel layer 6, therefore, should be composed of a material that is at least resistant to moisture and dirt, and other foreign matter that could adversely affect the adhesive. The peel layer 6 preferably comprises at least two separately peelable sections. In the embodiment where the peel layer 6 comprises two separately peelable sections, as indicated in FIG. 2, such sections are substantially equal in size. It is also envisioned that the peelable layer may be segmented into three or four sections wherein two of which would be separately peelable from the cannula engaging portions 3a and 3b.

The nasal cannula anchor of the present invention is preferably used to anchor a oxygen cannula 10. An oxygen cannula as used herein comprises two lengths of medical tube 11a and 11b joined together by a nasal fitting 12 having opposite ends to an end of each of the lengths of medical tubes, the opposite ends of the medical tubes being attached to another fitting (not shown) which in turn is connected to another tube (not shown) in communication with a source of oxygen (not shown). The nasal fitting is provided with two ports which are located substantially in the middle between the opposite ends of the nasal fitting. Each of these ports preferably has a spout-like form 13a and 13b and the ports are spaced apart from each other and otherwise configured to be inserted into the nostrils of a patient for discharging oxygen into the nostrils of the patient. The two legs or tube engaging portions 3a and 3b of the nasal cannula anchor of the present invention are configured to be wrapped or otherwise secured around a respective length of medical tube, or around sections of the nasal fitting at its opposite ends so as to anchor the nasal cannula to the nose and face of the patient in a proper position that will benefit the patient most.

The nasal cannula anchoring apparatus of the present invention may be cut out in the appropriate shape from a sheet or roll of dermaFLEX material. The trademark dermaFLEX is a trademark of FLEXcon Company, Inc. The most preferred material is dermaFLEX PE-225-CM GLEAM EMBOSSED H-566 90 PFW. This material is a flexible clear matte gleam embossed polyethylene film coated with a permanent pressure sensitive acrylic adhesive and backed with a two side poly coated layflat release liner. This material was initially used for resting electro cardiograph (ECG) electrodes surgical drapes and medical device where skin contact, conformability and flexibility are required. Other characteristics for materials suitable for purposes of the present invention are listed below:

| | |
|---|---|
| o Anti-glare | o Non-cytotoxic |
| o Very comfortable | o Non-sensitizing |
| o Meets USP Class 6 | o Hypoallergenic |
| o Non-irritating in both animals and humans | o Satisfies Tri-Partite guidelines for all skin contact devices |

The most preferred material for purposes of the present invention are tabulated below:

| PRODUCT DATA | VALUE | | | | TEST METHOD |
|---|---|---|---|---|---|
| | PHYSICAL PROPERTIES | | | | |
| Thickness [mils(microns)] | Film: 2.6 (66) +/− 15% | | | | ASTM D 1593 |
| | Adhesive: 1.4–1.5 (36–38) +/− 0.1 (3) | | | | |
| | Liner: 6.7 (170) +/− 10% | | | | |
| | ADHESION PROPERTIES | | | | |
| | Average | | Expected Range | | |
| | oz/in | (N/m) | oz/in | (N/m) | |
| Immediate Peal | 30 | (330) | 20–45 | (220–495) | PSTC 1 |
| Tack (gm/sq cm) | 550 | | 300–800 | | ASTM D 2979-71 |

In accordance with the present invention, a method is provided for anchoring a length of cannula in the nose of a subject that involves wrapping the two cannula engaging portions extending from the body engaging portion of the nasal cannula anchor of the present invention as described herein around a section of length of a cannula or a nasal cannula fitting and adhering the body engaging portion of the nasal cannula anchor of the present invention to the nose of a subject to anchor the cannula.

Prior to doing so, the nasal cannula anchor is removed from any packaging in which it may be contained. Preferably the peel strip layer is removed to expose the adhesive coating on the two cannula engaging portions extending from the body engaging portion of the nasal cannula anchor at which time the two cannula engaging portions are ready to be wrapped around a section of length of a cannula or a nasal cannula fitting. The remaining peel strip layer is then removed from at least a portion of the body engaging portion of the nasal cannula anchor which is then contacted with the nose of the subject, preferably near its tip with the trailing edge of the body engaging portion of the nasal cannula anchor being kept clear of the nostrils, and pressed thereagainst so as to adhere to the nose and anchor the nasal cannula in a secure position.

Having thereby described the subject matter of the present invention, it should be apparent that many substitutions, modifications and variations of the invention are possible in light of the above teachings. It is therefore to be understood that the invention as taught and described herein is only to be limited to the extent of the breadth and scope of the appended claims.

What is claimed is:

1. A nasal cannula anchor comprising:

a structure for anchoring a length of cannula to the nose of a subject, said structure being cut from a sheet of flexible material comprising:

a nose engaging portion that is adapted to adhere to the nose of a subject; and two cannula engaging portions extending from said body engaging portion that are adapted to anchor a cannula, wherein said body engaging portion said two cannula engaging portions of said structure comprise a plurality of layers comprising:

a patch layer;

an adhesive covering at least a portion of said patch layer; and a protective peel strip layer;

wherein said cannula engaging portions are wrappable around a cannula after said protective peel strip layer is removed.

2. The nasal cannula anchor apparatus of claim 1, wherein said body engaging portion comprises a substantially curved leading edge adapted to be oriented towards the bridge of the nose when said body engaging portion is adhered to the nose of a subject.

3. The nasal cannula anchor apparatus of claim 2, wherein said body engaging portion further comprises a trailing edge opposite said substantially curved edge adapted to be oriented away from the bridge of the nose when said body engaging portion is adhered to the nose of a subject.

4. The nasal cannula anchor apparatus of claim 3, wherein said trailing edge comprises a substantially straight central section adapted to be clear of nasal passages when said body engaging portion is adhered to the nose of a subject.

5. The nasal cannula anchor apparatus of claim 4, wherein said two cannula engaging portions extending from said body engaging portion are separated from each other by said straight central section of said trailing edge.

6. The nasal cannula anchor apparatus of claim 1, wherein said patch layer comprises a polyethylene material.

7. The nasal cannula anchor apparatus of claim 1, wherein said adhesive comprises hypoallergenic adhesives.

8. The nasal cannula anchor apparatus of claim 7, wherein said hypoallergenic adhesive comprise acrylic adhesives.

9. The nasal cannula anchor apparatus of claim 1, wherein said peel strip layer comprises a protective layer protecting said adhesive covering.

10. The nasal cannula anchor apparatus of claim 9, wherein said protective layer comprises a material that is at least resistant to moisture, dirt, and other foreign matter that could adversely affect said adhesive.

11. A method for anchoring a length of cannula in the nose of a subject, said method comprising:

providing a structure comprising a body engaging portion further comprising a patch layer and an adhesive covering at least a portion of said patch layer;

adhering said structure to the nose of a subject; and wrapping two cannula engaging portions comprising a patch layer and an adhesive covering at least a portion of said patch layer extending from said body engaging portion of said structure around a section of length of a cannula so as to adhesively attach said cannula engaging portions to anchor the cannula.

* * * * *